United States Patent
Basilice et al.

Patent Number: 5,848,999
Date of Patent: *Dec. 15, 1998

[54] DISPENSING EYE DROPS

[76] Inventors: Vincent P. Basilice, 2500-50 Nesconset Hwy., Bldg. 14, Stony Brook, N.Y. 11790; Joseph P. Basilice, 10 Landview Drive, Dix Hills, N.Y. 11746

[ * ] Notice: The term of this patent shall not extend beyond the expiration date of Pat. No. 5,366,448.

[21] Appl. No.: 292,502

[22] Filed: Aug. 18, 1994

Related U.S. Application Data

[63] Continuation of Ser. No. 081,351, Jun. 28, 1993, Pat. No. 5,366,442, which is a continuation-in-part of Ser. No. 871,100, Apr. 20, 1992, abandoned.

[51] Int. Cl.⁶ ................................................. A61M 35/00
[52] U.S. Cl. ..................... 604/300; 604/290; 604/302; 222/420
[58] Field of Search .............. 604/290, 294–302; 222/420–422, 215

[56] References Cited

U.S. PATENT DOCUMENTS

| | | | |
|---|---|---|---|
| 3,279,466 | 10/1966 | Mings | 128/233 |
| 3,598,121 | 8/1971 | Lelicoff | 604/302 |
| 3,872,866 | 3/1975 | Lelicoff | 604/302 |
| 3,934,590 | 1/1976 | Campagna et al. | 128/233 |
| 4,531,944 | 7/1985 | Bechtle | 604/302 |
| 4,605,398 | 8/1986 | Herrick | 604/300 |
| 4,792,334 | 12/1988 | Py | 604/301 |
| 5,007,905 | 4/1991 | Bauer | 604/295 |
| 5,030,214 | 7/1991 | Spector | 604/301 |
| 5,059,188 | 10/1991 | Goddard | 604/300 |
| 5,154,711 | 10/1992 | Williams | 604/301 |
| 5,267,986 | 12/1993 | Py | 604/294 |

*Primary Examiner*—Mary Beth Jones
*Attorney, Agent, or Firm*—Rader, Fishman & Grauer, PLLC

[57] ABSTRACT

An eye drop dispensing device (10), designed to replace the cap (18) of an eye drop squeeze bottle (12), includes a positioning member (38). The positioning member is brought to bear against a boundary (54) of a patient's (14) lower eyelid (36), and the assembly (52) rotated about the member to bring a nozzle tip (24) of the device in facing relation with the eye (32). Besides providing stability to the assembly, the member assists in the eversion of the lower eyelid to form a well-like configuration (61) to receive drops (28). Thus, the patient may maintain a primary gaze position (17), facilitating the eye drop dispensing procedure.

7 Claims, 2 Drawing Sheets

5,848,999

DISPENSING EYE DROPS

This is a continuation of application Ser. No. 08/081,351 filed on Jun. 28, 1993, now U.S. Pat. No. 5,366,442, which is a continuation in part of U.S. application Ser. No. 07/871,100, filed on Apr. 20, 1992, now abandoned.

BACKGROUND OF THE INVENTION

The present invention relates generally to improvements for facilitating the dispensing of eye drops, the improvements more particularly obviating such prior art shortcomings as requiring a tilted-back head position, preventing inadvertent blinking and other occurrences during administration of the eye drops which are counterproductive to achieving the purposes intended.

It is already part of prior art practice employing commercially available squeeze bottle or equivalent eye drop dispensers to use positioning devices to direct the dispensed eye drops onto the eye surface where needed. Such positioning devices are exemplified by the tripod support of Campagna, et al. of U.S. Pat. No. 3,934,590, issued on Jan. 27, 1976, and the eye-encircling dispenser support of Bechtle of U.S. Pat. No. 4,531,944, issued on Jul. 30, 1985. These, and all other known prior art combined supports and dispensers, while beneficial, still have shortcomings. Such shortcomings include requiring special head positions and other special procedures or techniques that, at best, make self-application difficult and, more often, prevent the user from achieving proper eye treatment using eye drops. The prior art dispensers can sometimes even contribute to the spreading of the eye infection with an inadvertently contaminated dispenser.

The present invention is intended to provide a safe and effective eye drop dispensing method and components for its practice, overcoming the foregoing and other shortcomings of the prior art. Using the present invention, eye drops are more efficiently administered, reducing waste. This is of particular importance with certain medicinal eye drops, which are particularly expensive. Further, the present invention dispenses eye drops with the recipient's or patient's head in a natural position and otherwise with such ease that self-application is possible. As such, the present invention may be used even by the elderly and by patients with poor eyesight, crippling arthritis or other heretofore interfering handicaps.

SUMMARY OF THE INVENTION

An improved eye drop assembly includes an inventive dispensing device secured to an eye drop dispenser. An improved method of administering drops of fluid medication allows a patient to maintain their head in an erect orientation.

The eye drop dispensing device includes a cylindrical, dome-shaped collar. The collar has an opening extending along a collar axis adapted to receive a dispenser nozzle of the dispenser and internal threads adapted to engage corresponding external threads on the dispenser.

A positioning member is attached to and extends away from the collar. The positioning member assists in an eversion of a lower eyelid of a patient to form a bowed configuration suitable to receive drops. Further, the positioning member is sized to act as a point upon which the assembly may pivot such that in an operative orientation, drops from the dispenser may be received by the bowed configuration of the lower eye lid. This greatly reduces fluid medication waste while simultaneously increasing the ease with which patients may deliver their own drops.

BRIEF DESCRIPTION OF THE DRAWINGS

The description of the invention which follows, together with the accompanying drawings should not be construed as limiting the invention to the example shown and described, because those skilled in the art to which this invention appertains will be able to devise other forms thereof within the ambit of the appended claims:

DETAILED DESCRIPTION OF A PREFERRED EMBODIMENT

Figure 1:
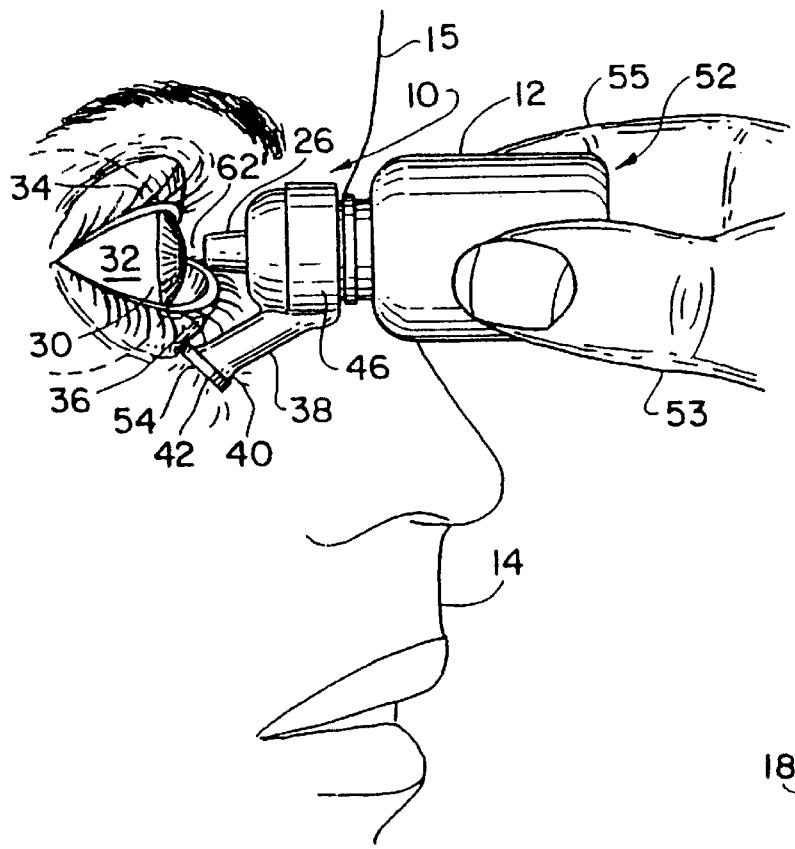
FIG. 1 is a side elevational view of a known, commonly-called squeeze bottle eye drop dispenser in assembled relation to an inventive eye drop dispensing device member in an operative position preparatory to use according to the present invention.
Figure 3:
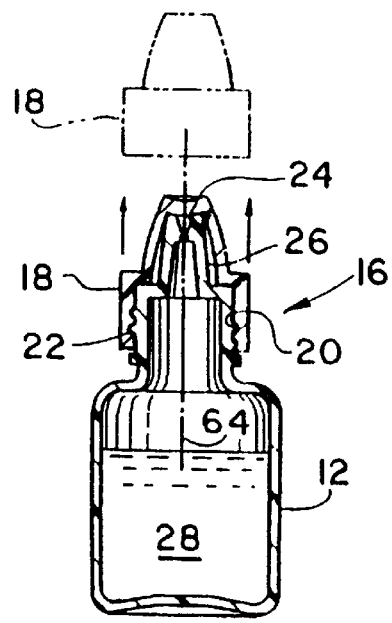
FIG. 3 is a prior art figure showing in an isolated cross-section a popular squeeze bottle eye drop dispenser in current use that may be utilized for use in accordance with the inventive eye drop dispensing apparatus and method.
Figure 4:
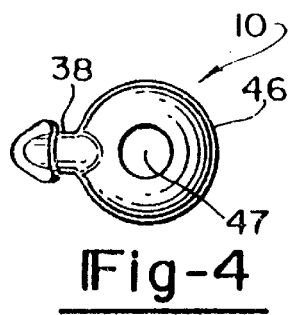
FIGS. 4, 5 and 6 are respectively plan, side and front elevational views of the inventive eye drop dispensing device prior to the squeeze bottle being assembled thereto.
Figure 9:
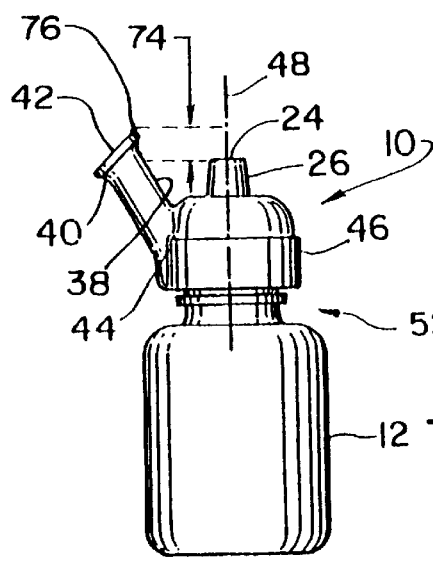
FIG. 9 is a side elevational view of the eye drop dispensing device of FIGS. 4, 5 and 6 in assembled relation with the squeeze bottle eye drop dispenser of FIG. 3.

An assemblage 52 of a preferred embodiment of an eye drop dispensing device 10 is illustrated in FIGS. 1 and 9. Dispensing device 10 is assembled to a standard eye drop dispenser squeeze bottle 12 and in a first operative position 54 preparatory to use by a patient 14. That is, and understood to be used almost exclusively, is a popular present day eye drop dispenser 16, herein shown in the prior art FIG. 3, which consists of a pliable or squeezable plastic bottle 12 with removable cap member 18. Cap 18 has internal threads 20 of an appropriate selected pitch to engage external threads 22 on bottle 12. Cap 18 is sized to seal the outlet opening 24 of the bottle dispenser nozzle 26 when threads 20, 22 are threadably engaged. Bottle 12 in practice is usually commercially sold in a ½ fluid ounce size, and is of flexible plastic and, of course, of any convenient shape appropriate to store fluid medication 28.

In the prior art, when using bottle 12 to apply medication 28 to a surface 30, i.e. the cornea/sclera, of an eyeball 32, the patient 14 was required to tilt his/her head 15 "all the way back" or even to assume the supine position. Bottle 12, with cap 18 removed is then inverted and from an above clearance position above the target eye 32, the patient 14 attempts to "squeeze off" a single drop of medication 28. As often inadvertently happens, however, the drop misses the eye surface 30 completely, or the patient yields to a reflex action and blinks covering the eye surface 30 and consequently wasting the medication 28. In attempting to position bottle 12 properly above eye 32, another prior art shortcoming may result from the patient touching the infected surface 30 or eyelids 34, 36 and causing contamination of the dispensing outlet which can result in reinfection of eye 32 as subsequent doses are applied.

Figure 5:
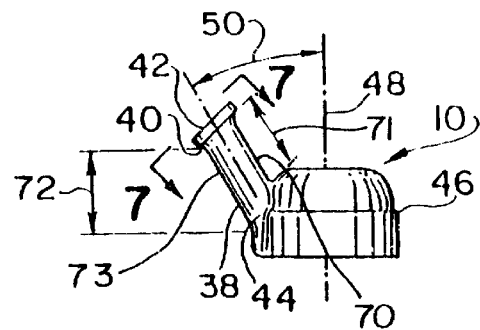
Figure 6:
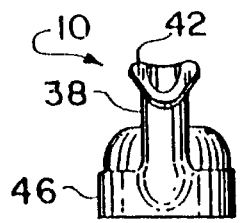
Figure 7:
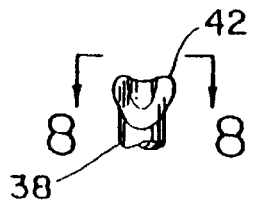
FIG. 7 is a partial detail view as taken along line 7—7 of FIG. 5.
Figure 8:
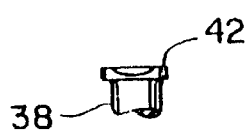
FIG. 8 is a partial detail view as taken along line 8—8 of FIG. 7.

The dispensing device 10, as shown in FIGS. 4, 5, 6 and 7, is comprised in part of a positioning member 38 whose outer or unattached end 40 is provided with a somewhat triangular, contoured pad 42 having a suction-like cup design, as best seen in FIGS. 5, 7 and 8, to facilitate the engagement of end 40 with the patient's lower eyelid 36. (See FIGS. 1 and 9). At its opposite or inner end 44, member 38 is joined to a cylindrical dome-shaped collar 46. Collar 46 is constructed with internal threads 20 of a selected pitch to readily engage external threads 22 on bottle 12 after cap 18 has been removed. Collar 46 also includes an opening 47 extending along a collar axis 48, the opening 47 adapted to receive dispenser nozzle 26 of bottle dispenser 12. In a preferred embodiment, device 10 is made from a flexible material such as rubber.

Figure 10:
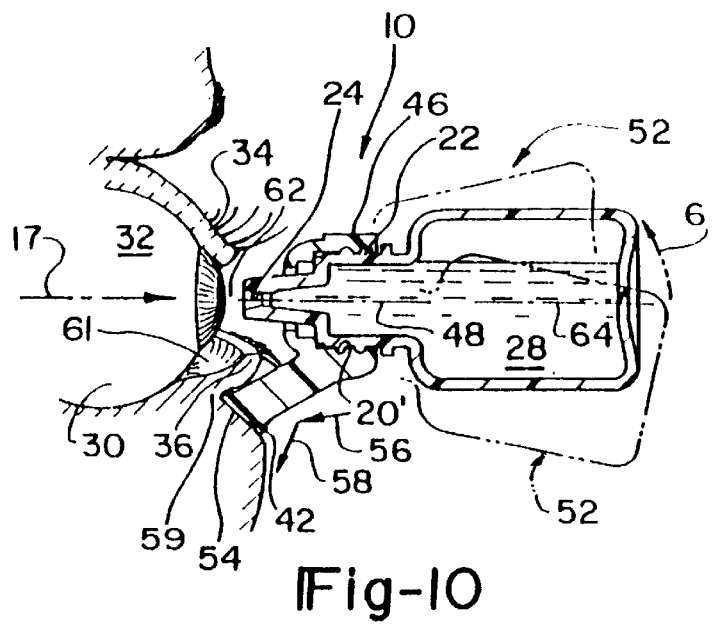
FIG. 10 is a view similar to FIG. 1, but shown in cross section as taken along line 10—10 of FIG. 2, and further showing respectively in phantom and full line perspective the positions of movement of the assembled eye drop dispenser of FIG. 9.

After cap 18 has been replaced by device 10 on bottle 12 providing the assembly 52 of FIG. 9, the assembly 52 is advantageously gripped and held between the thumb 53 and forefinger 55 of one hand and moved into the operative position of FIG. 1. The assembly 52, and especially pad 42 is brought to bear against the patient's eye lower boundary 54 of lower lid 36 at the tarsal palpebral area, as best shown in FIGS. 1 and 10. It is contemplated that assembly 52 will be moved with a combined motion inward along arrow 56 and downward along arrow 58 in conjunction with a careful rotation along a path 60 about member 38, to bring nozzle tip 24 of nozzle 26 to a clearance position 62 in facing relation to eye 32 of patient 14. Thus, member 38 provides stability to assembly 52. Nozzle 26 and nozzle tip 24 are used to dispense fluid medication 28. Clearance position 62 is defined approximately in FIG. 10 by the phantom perspective outline of assembly 52. A preferred clearance position 62 places tip 24 within 10 mm of corneal surface 30, adjacent eye 32 and most significantly above the now bowed or distended tarsal plate 59 of lower lid 36, which the movements 56 and 58 have effectively caused to undergo an eversion of approximately 3 to 4 mm to form an extended well-like or trough configuration 61. In a preferred embodiment only positioning member 38 extends away from dome shaped collar 46 to limit possible interference with the use of dispensing device 10.

To obtain the preferred clearance position 62 and desired eversion 61, it is preferred that positioning member 38 be angularly offset from collar axis 48 by an angle 50. The offset angle 50 is preferably between 10 and 80 degrees and most preferably approximately 30 degrees, as best shown in FIG. 5. Further, an upper outer surface 70 of positioning member 38 preferably has a dimension 71 extending approximately 19 mm away from collar 46, while a component of length 72 for lower outer surface 73, extending along collar axis 48, is approximately 28 mm. The distance between surfaces 70 and 73 is preferably approximately 7 mm. Finally, the axial displacement 74, measured along collar axis 48, between tip 24 and an edge 76 of pad 42 adjacent to tip 24, as shown in FIG. 9, is less than 10 mm, preferably within a range of between 3 and 5 mm, and most preferably at 4.5 mm.

Once tip 24 is placed in position 62, axis 48 of collar 46, and axis 64 of bottle 12 are now virtually parallel and possibly coincident with a primary gaze axis 17. (See FIG. 10). Preferably, assembly 52 is pivoted between 30 and 60 degrees beyond gaze axis 17, as shown in phantom in FIG. 10, so that tip 24 has an axial displacement within 1 mm of edge 76 as measured along gaze axis 17. Thus, the force of gravity may be used to promote the depositing of fluid medication 28 within the bowed configuration 61. Further, this operative orientation is preferred since, at the time of the administration of the eye drops, the patient's head is in an erect orientation most advantageous for this procedure, and is a head position to be distinguished from the prior art practice in which the patient's head is tilted back and the eye drops dispensed from an above clearance position directly onto the patient's eyeball or cornea/sclera surface 30.

The use of primary gaze axis 17 promotes the depositing of drops of fluid medication 28 behind the patient's lower eyelid 36, which has effectively previously undergone eversion to present bowed configuration 61 suitable for receiving drops of fluid medication 28 from outlet opening 24. Obviated is the prior art shortcoming in which the eye drop is administered off-target, or the patient yields to the reflex action of blinking and thus blocking the eye drop from making contact with the eye surface. This reduces waste, which is of particular importance when using certain very expensive medicinal fluid medications 28. The patient 14 is not required to assume an ungainly head position and is much less likely to blink as in the prior art. By virtue of the ease of eye drop administration or application in accordance with the present invention, even elderly patients or patients with poor eyesight or crippling arthritis can now deliver their own eye drops, not relying on others for assistance, which will promote patient confidence and compliance.

Figure 2:
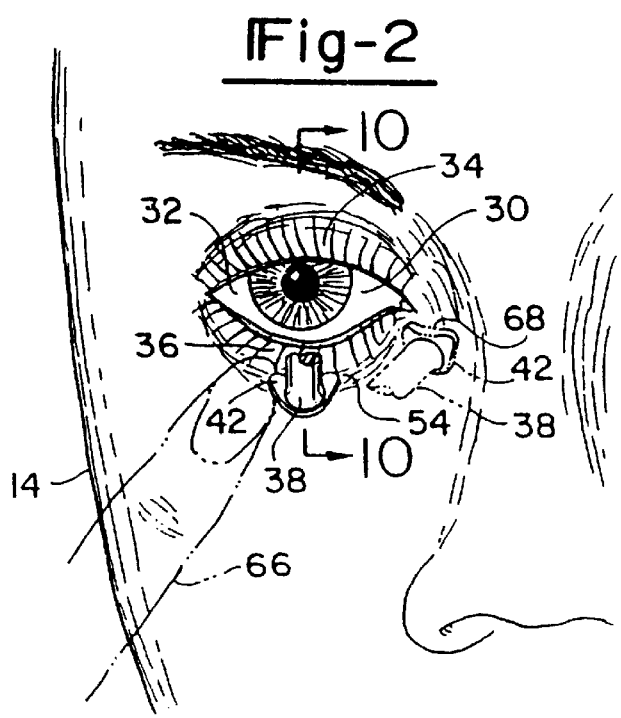
FIG. 2 is a partial front view of a patient's face that best illustrates the FIG. 1 operative position or location of the present dispensing device when in use.

As illustrated in FIG. 2, a prepositioning of the index finger 66 of the patient's free hand is recommended to help accomplish the bowing of lower lid 36. With assembly 52 held in this relation to bowed lid 36, medication 28 is now ready to be dispensed within the extended well-like or trough configuration 61 of lid 36, one drop at a time.

In an alternative embodiment, it is envisioned that bottle 12 may include a portion of the structure of dispensing device 10. For example, positioning arm 38 may be integral to the bottle 12.

For completeness sake it is noted that, after the drop delivery is completed, the patient 14 preferably removes the assembly 52 and relocates pad 42 at the inferior punctum 68, which is at the juncture of nose 69 and lower lid 36, as best shown in FIG. 2. By maintaining slight pressure for about one minute at the inferior punctum 68, as is well understood, slows the runoff of medication 28 by occluding the common caniculuor canal.

Preferred embodiments of the present invention have been described. It is to be understood that variations and modifications may be employed without departing from the scope of the present invention. Accordingly, the following claims should be studied to determine the true scope of the present invention.

We claim:

1. An eye drop dispensing device for a squeeze bottle dispenser for administering fluid eye medication in drop dosages to an eye of a patient, said device comprising:

a cylindrical, dome-shaped collar, said collar including an opening extending along a collar axis, said opening adapted to receive a dispenser nozzle of the dispenser;

attachment means to secure said collar to the dispenser; and a positioning means for assisting in an eversion of a lower eyelid to form a bowed configuration suitable to receive drops of the medication deposited from an outlet opening when the patient's head is in an erect orientation to provide a corresponding horizontal primary gaze position to a patient's eye selected to receive medication, the dispensed eye drop dropping vertically from the outlet opening to contact the bowed configuration of the eyelid before any contact with the eye, said positioning means extending away from said collar and including an outer end such that an axial displacement measured along said collar axis, between an edge of said outer end of said positioning means adjacent the outlet opening when the dispenser is attached to said device, and the outlet opening, is less than about 10 mm.

2. An eye drop dispenser device as recited in claim 1, wherein said outer end of said positioning member includes a pad adapted to engage a lower boundary of the lower eyelid.

3. An eye drop dispenser as recited in claim 2, wherein said pad is contoured to correspond to a lower boundary of the lower eyelid.

4. An eye drop dispenser device as recited in claim 1, wherein said attachment means comprises internal threads, said threads disposed within said collar and adapted to engage corresponding external threads on the dispenser.

5. An eye drop dispenser device as recited in claim 1, wherein said axial displacement is between 3 and 5 mm.

6. An eye drop dispenser device as recited in claim 1, wherein said device includes only one said positioning member.

7. An eye drop dispenser device as recited in claim 1, wherein said positioning member extends away from said collar at an angle offset from said axis, said angle between said positioning member and said axis being between 10 and 80 degrees.

* * * * *